US010420527B2

(12) United States Patent
Misra et al.

(10) Patent No.: US 10,420,527 B2
(45) Date of Patent: Sep. 24, 2019

(54) DETERMINING A HEART RATE AND A HEART RATE VARIABILITY

(71) Applicant: Tata Consultancy Services Limited, Mumbai (IN)

(72) Inventors: Aditi Misra, Kolkata (IN); Aniruddha Sinha, Kolkata (IN); Avik Ghose, Kolkata (IN); Anirban Dutta Choudhury, Kolkata (IN); Rohan Banerjee, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 331 days.

(21) Appl. No.: 15/098,254

(22) Filed: Apr. 13, 2016

(65) Prior Publication Data

US 2016/0302732 A1    Oct. 20, 2016

(30) Foreign Application Priority Data

Apr. 14, 2015   (IN) .......................... 1544/MUM/2015

(51) Int. Cl.
*A61B 5/00*   (2006.01)
*A61B 7/04*   (2006.01)
(Continued)

(52) U.S. Cl.
CPC ............ *A61B 7/045* (2013.01); *A61B 5/7253* (2013.01); *A61B 7/00* (2013.01); *A61B 5/024* (2013.01);
(Continued)

(58) Field of Classification Search
CPC ... A61B 5/024; A61B 5/02405; A61B 5/0255; A61B 5/7235; A61B 5/725; A61B 5/7253; A61B 5/7264; A61B 7/04; A61B 7/045
See application file for complete search history.

(56) References Cited

U.S. PATENT DOCUMENTS

| 7,130,429 | B1* | 10/2006 | Dalgaard | ................. A61B 7/04 381/67 |
| 2009/0275849 | A1* | 11/2009 | Stewart | ............. A61B 5/02405 600/518 |

FOREIGN PATENT DOCUMENTS

| CN | 203828916 | 9/2014 |
| CN | 104367344 | 2/2015 |

(Continued)

OTHER PUBLICATIONS

Ruffo et al. "An algorithm for FHR estimation from foetal phonocardiographic signals". Biomedical Signal Processing and Control, vol. 5, Issue 2, Apr. 2010, pp. 131-141.*

(Continued)

*Primary Examiner* — Eugene T Wu
(74) *Attorney, Agent, or Firm* — Finnegan, Henderson, Farabow, Garrett & Dunner LLP (57) ABSTRACT

System and method for determining a heart rate and a heart rate variability of an individual is disclosed. An audio signal of heart sound is amplified. Subsequently, an envelope of the amplified audio signal is detected by squaring of the amplified audio signal to obtain emphasized high amplitude components and diminished low amplitude components of the audio signal, applying a band pass filter on the audio signal upon squaring and applying a Teager-Kaiser Energy Operator (TKEO) on the filtered audio signal. Peaks in the envelope of the audio signal are detected by calculating difference in magnitude of a point in the audio signal with an average of magnitude of earlier points in the audio signal from the last detected peak or the initial sample value in the processing window when no peak is detected. Based on the peaks detected, heart rate and heart rate variability for the individual are determined.

10 Claims, 9 Drawing Sheets

(51) Int. Cl.
*A61B 7/00* (2006.01)
*A61B 5/024* (2006.01)

(52) U.S. Cl.
CPC ......... *A61B 5/02405* (2013.01); *A61B 5/6898* (2013.01); *A61B 5/7235* (2013.01); *A61B 5/7282* (2013.01)

(56) References Cited

FOREIGN PATENT DOCUMENTS

| KR | 10-2014-0092099 | 7/2014 |
|---|---|---|
| WO | WO-2012/133931 | 10/2012 |

OTHER PUBLICATIONS

Jiang et al. "A cardiac sound characteristic waveform method for in-home heart disorder monitoring with electric stethoscope". Expert Systems with Applications, vol. 31, Issue 2, Aug. 2006, pp. 286-298.*

Oweis et al. "Heart Sounds Segmentation Utilizing Teager Energy Operator". Journal of Medical Imaging and Health Informatics. 4. 10.1166/jmihi.2014.1292.*

Zahorian et al. "Dual transmission model and related spectral content of the fetal heart sounds". Computer Methods and Programs in Biomedicine, vol. 108, Issue 1, Oct. 2012, pp. 20-27.*

S. S. Mehta, S. Sharma and N. S. Lingayat, "Development of FCM based algorithm for the delineation of QRS-complexes in Electrocardiogram," 2009 World Congress on Nature & Biologically Inspired Computing (NaBIC), Coimbatore, 2009, pp. 754-759.*

Kuan, K.L. (Jul. 2010). *A Framework for Automated Heart and Lung Sound Analysis Using a Mobile Telemedicine Platform* (Master's thesis, Massachusetts Institute of Technology). Retrieved from http://www.robots.ox.ac.uk/~garl/papers/KuanThesis2010.pdf; 261 pages.

Kumar, D. et al. (Apr. 2011) "Noise detection during heart sound recording using periodicity signatures," *Physioogical Measurement*, vol 32, pp. 599-618.

* cited by examiner

DETERMINING A HEART RATE AND A HEART RATE VARIABILITY

PRIORITY CLAIM

This U.S. patent application claims priority under 35 U.S.C. § 119 to: India Application No. 1544/MUM/2015 filed on 14 Apr. 2015. The entire contents of the aforementioned application are incorporated herein by reference.

TECHNICAL FIELD

The present disclosure in general relates to a field of determining heart rate and heart rate variability. More particularly, the present disclosure relates to a system and a method for determining a heart rate and a heart rate variability using a microphone of an electronic device.

BACKGROUND

Heart rate is a speed of heart beat measured by number of poundings of the heart per unit of time. Typically, the heart rate is measured in Beats per Minute (BPM). The heart rate may vary according to body of an individual, including absorption of oxygen and excretion of carbon dioxide. Heart rate variability (HRV) is a physiological phenomenon of variation in a time interval between the heartbeats. Typically, the HRV may be measured by the variation in the beat-to-beat interval.

There exist solutions to determine heart rate and heart rate variability (HRV) of the individual using an electronic device. Typically, the existing solutions use a concept of photoplethysmography or ECG to determine heart rate and heart rate variability (HRV). Generally, the photoplethysmography is well suited for determining the heart rate, however fails to determine the HRV accurately due to low temporal resolution. Another solution offered is use of a digital stethoscope to capture the heartbeat sounds for extracting the heart rate and HRV of the individual. In spite of providing high temporal resolution (44.1 kHz sampling rate), the solution is susceptible to mechanical friction, ambient sounds, audio feedback and noise is generated by the electronic circuits. In order to eliminate the noise, noise cancellation technique is used by applying a low-pass filter on an audio signal. However, the noise cancellation technique cannot eliminate the noise components present in the pass band. Therefore, frequency domain representation often fails to detect the heart rate accurately due to abrupt change in dominant peak location.

SUMMARY

Embodiments of the present disclosure present technological improvements as solutions to one or more of the above-mentioned technical problems recognized by the inventors in conventional systems.

In one implementation, a method for determining a heart rate and a heart rate variability of an individual is disclosed. The method comprises capturing heart sound of an individual. The method further comprises amplifying, by a processor, an audio signal of the heart sound. The method further comprises detecting, by the processor, an envelope of the amplified audio signal. The envelope of the amplified audio signal is detected by squaring of the amplified audio signal to obtain emphasized high amplitude components and diminished low amplitude components of the audio signal, applying a band pass filter on the audio signal upon squaring and applying a Teager-Kaiser Energy Operator (TKEO) on the audio signal filtered. The method further comprises detecting, by the processor, peaks in the envelope of the audio signal. The peaks are detected by calculating difference in magnitude of a point in the audio signal with an average of magnitude of earlier points in the audio signal from last detected peak or initial sample value in processing window of the audio signal when no peak is detected. The method further comprises determining, by the processor, a heart rate and a heart rate variability for the individual using the peaks detected. The method further comprises classifying the peaks detected into three clusters using a k-means clustering algorithm. The heart rate of the individual is determined based on the difference of consecutive peaks. The difference corresponds to an average time period of heart beat. The heart rate is determined by calculating an inverse of the difference of consecutive peaks. The heart rate variability is determined based on the difference of consecutive peaks.

In one implementation, a system for determining a heart rate and a heart rate variability of an individual is disclosed. The system comprises a memory and a processor coupled to the memory. The processor executes program instructions stored in the memory to capture heart sound of an individual. The processor further executes the program instructions to amplify an audio signal of the heart sound. The processor further executes the program instructions to detect an envelope of the amplified audio signal. The envelope of the amplified audio signal is detected by squaring the amplified audio signal to obtain emphasized high amplitude components and diminished low amplitude components of the audio signal, applying a band pass filter on the audio signal upon squaring and applying the Teager-Kaiser Energy Operator (TKEO) on the audio signal filtered to obtain the envelope of the audio signal. The processor further executes the program instructions to detect peaks in the envelope of the audio signal. The peaks are detected by calculating difference in magnitude of a point in the audio signal with an average of magnitude of earlier points in the audio signal from last detected peak or initial sample value in processing window of the audio signal when no peak is detected. The processor further executes the program instructions to determine a heart rate and a heart rate variability for the individual using the peaks detected. The heart rate of the individual is estimated based on the difference of consecutive peaks. The heart rate variability is determined based on the difference of consecutive peaks. The processor further executes the program instructions to cluster a distance between the peaks detected using a Fuzzy C Means (FCM) clustering algorithm. The FCM clustering algorithm is used to remove false positive peaks and to add false negative peaks. The false negative peaks are removed by calculating a mean and a standard deviation corresponding to the distance between the peaks. The processor further executes the program instructions to classify the peaks detected into three clusters using a k-means clustering algorithm.

In one implementation, a computer program product comprising a non-transitory computer readable medium having a computer readable program embodied therein is disclosed, wherein the computer readable program, when executed on a computing device, causes the computing device to: capture heart sound of an individual; amplify an audio signal of the heart sound; detect an envelope of the amplified audio signal, wherein the envelope of the amplified audio signal is detected by; squaring of the amplified audio signal to obtain emphasized high amplitude components and diminished low amplitude components of the audio signal; applying a band pass filter (0.7-3.6 Hz) on the audio signal upon squaring; and applying a Teager-Kaiser Energy Operator (TKEO) on the audio signal filtered to obtain the envelope of the audio signal; detect peaks in the envelope of the audio signal, wherein the peaks are detected by calculating difference in magnitude of a point in the audio signal with an average of magnitude of earlier points in the audio signal from last detected peak or initial sample value in the processing window of the audio signal when no peak is detected; and determine a heart rate and a heart rate variability for the individual using the peaks detected.

It is to be understood that both the foregoing general description and the following detailed description are exemplary and explanatory only and are not restrictive of the invention, as claimed.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like/similar features and components.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present disclosure relates to a system and a method for determining a heart rate and a heart rate variability of an individual. At first, heart sound of the individual may be captured. The heart sound may be captured using a microphone of a smart phone. After capturing the heart sound, an audio signal of the heart sound may be amplified to make the audio signal audible. The audio signal may be amplified as the amplitude of the heart sound may be low. Subsequently, an envelope of the amplified audio signal may be detected. The envelope of the amplified audio signal may be detected by taking a square of the audio signal in order to emphasize high amplitude components and diminish low amplitude components of the amplified audio signal. Further, a band pass filter may be applied on the audio signal. Specifically, a second order Butterworth band pass filter may be applied on the audio signal. Subsequently, a Teager-Kaiser Energy Operator (TKEO) may be applied on the audio signal amplified, squared and band passed.

After detecting the envelope of the audio signal, an average of magnitude of all earlier points is calculated. Subsequently, a magnitude of a current point subsequent to the magnitude of points averaged in the audio signal is detected from the last detected peak or the initial sample value in the processing window when no peak is detected. Further, difference in the magnitude of the current point and the average of the earlier points is calculated to detect the peaks in the envelope. If the difference is greater than zero and the amplitude of a subsequent point following the current point's amplitude is equal or less, the current point is considered as the peak.

After the peaks are detected, the peaks may be enumerated and an FCM clustering algorithm is run on the peak to peak distance to classify the peak to peak distances. Specifically, the peaks are classified as a cluster comprising of smaller peak to peak distances and a cluster comprising of higher peak to peak distances. Subsequently, false negative peaks are removed from the detected peaks. After removing the false negative peaks, differences in consecutive peaks are detected. The average consecutive difference corresponds to an average time period of heart beat. After obtaining the average time period of heart beat, a reciprocal of the average time period of heart beat may be calculated to estimate the average heart rate of the individual.

Further, a heart rate variability may be determined based on the difference of the consecutive peaks detected. Specifically, the heart rate variability may be determined using time domain metrics on the peaks detected.

While aspects of described system and method for determining a heart rate and a heart rate variability of an individual may be implemented in any number of different computing systems, environments, and/or configurations, the embodiments are described in the context of the following exemplary system.

Figure 1:
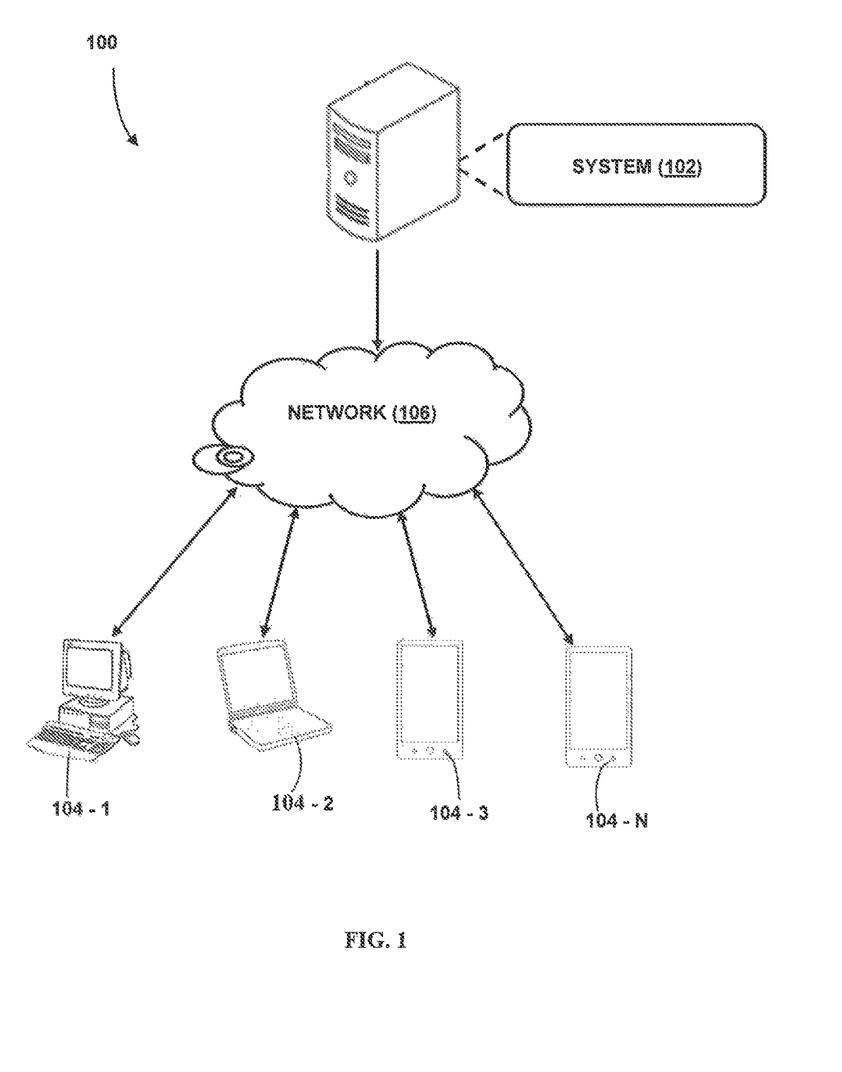
FIG. 1 illustrates a network implementation of a system for determining a heart rate and a heart rate variability of an individual, in accordance with an embodiment of the present disclosure.

Referring now to FIG. 1, a network implementation 100 of a system 102 for determining a heart rate and a heart rate variability of an individual is illustrated, in accordance with an embodiment of the present disclosure. The system 102 may capture heart sound of an individual. The system 102 may amplify an audio signal of the heart sound captured. Based on the audio signal amplified, the system 102 may detect an envelope of the amplified audio signal. The system 102 may detect the envelope of the audio signal by squaring of the amplified audio signal to obtain emphasized high amplitude components and diminished low amplitude components of the audio signal, applying a band pass filter on the audio signal upon squaring and applying a Teager-Kaiser Energy Operator (TKEO) on the filtered audio signal. Further, the system 102 may detect peaks in the envelope of the audio signal. The system 102 may detect the peaks in the envelope of the audio signal by calculating difference in magnitude of a point in the audio signal with an average of magnitude of earlier points in the audio signal from the last detected peak or initial sample value in processing window of the audio signal when no peak is detected. Based on the peaks detected, the system 102 may calculate a heart rate and a heart rate variability for the individual. Specifically, the system 102 may determine the heart rate and the heart rate variability based on differences of consecutive peaks detected.

Although the present disclosure is explained by considering that the system 102 is implemented on a server, it may be understood that the system 102 may also be implemented in a variety of computing systems, such as a laptop computer, a desktop computer, a notebook, a workstation, a mainframe computer, a server, a network server, cloud, and the like. It will be understood that the system 102 may be accessed by multiple users through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
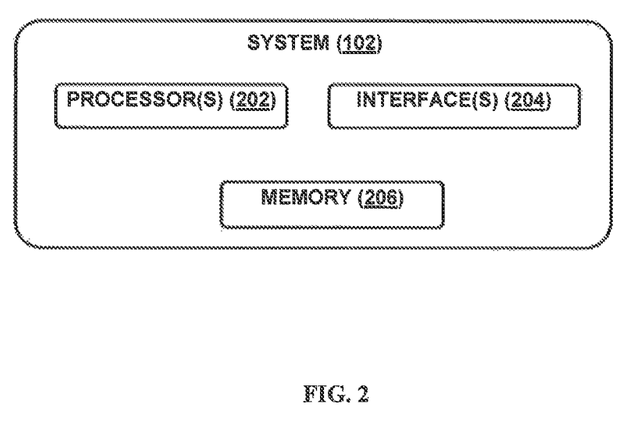
FIG. 2 illustrates the system, in accordance with an embodiment of the present disclosure.

Referring now to FIG. 2, the system 102 is illustrated in accordance with an embodiment of the present disclosure. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with a user directly or through the user devices 104. Further, the I/O interface 204 may enable the system 102 to communicate with other computing devices, such as web servers and external data servers (not shown). The I/O interface 204 may facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

In one implementation, at first, the user may use the client device 104 to access the system 102 via the I/O interface 204. The working of the system 102 may be explained in detail using FIG. 3 to FIG. 8. The system 102 may be used for determining a heart rate and a heart rate variability of an individual. For determining the heart rate and the heart rate variability, heart sound of the individual may be captured. The heart sound may be captured using an electronic device. Specifically, the electronic device may capture the heart sound using a microphone embedded in it. In one example, the electronic device may include, but not limited to, a smartphone, a tablet, a computer, and a wrist band such as a wrist watch. It should be understood that any electronic device that comprises a microphone may be used to capture the heart sound. Further, a digital stethoscope may be used to capture the heart sound.

Figure 3:
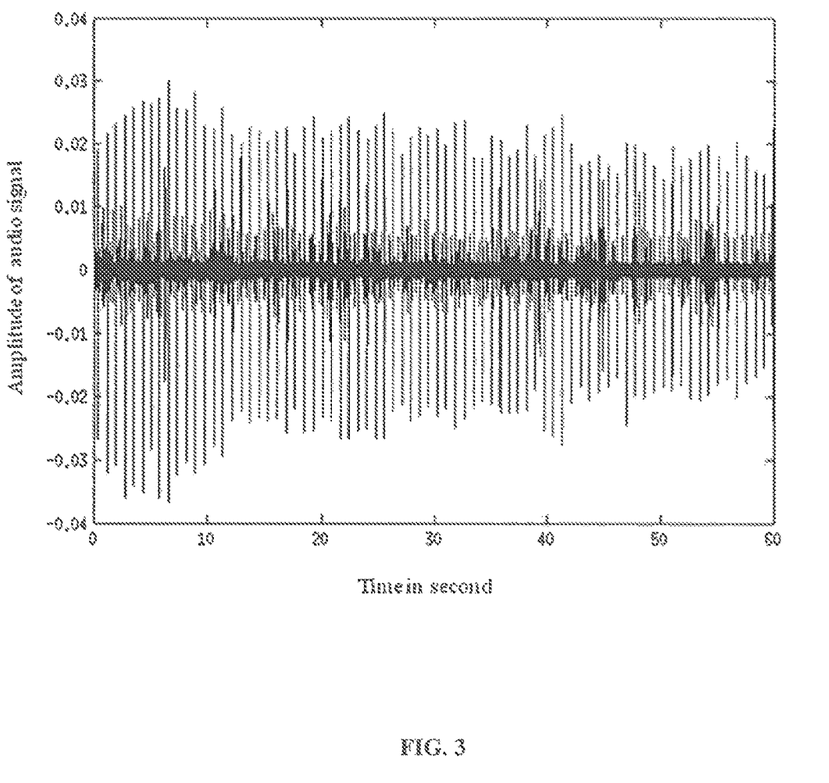
FIG. 3 shows heart sound captured without amplification, in accordance with an embodiment of the present disclosure.

In order to capture the heart sound, the electronic device may be placed close to heart of the individual. Specifically, the electronic device, e.g., a smartphone may be positioned slightly inward to mid-clavicular line on the third or fifth intercostal region on chest of the individual. When the electronic device is placed close to the third or fifth intercostal region on the chest, the microphone of the electronic device may capture the heart sound. The microphone may capture the first heart sound that is louder than the second heart sound if the phone is positioned at the fifth intercostal space and vice-versa when the microphone is positioned at third intercostal space. As the heart sound is captured when the electronic device is kept close to the chest, the heart sound captured may have noise and the heart sound may be low in amplitude. The noise may be an ambience noise. Due to the noise, it may be difficult to hear the heart sound. In order to capture the heart sound, i.e., heart beating sound, LUBB and DUB properly, an audio signal of the heart sound may need to be amplified. Specifically, the audio signal may be amplified in software level such that the audio signal does not exceed an audio bit depth supported by an audio file format in the capturing device, such as the electronic device. Further, the audio signal may be amplified for guiding the individual to place the microphone of the electronic device approximately about a region close to the heart where the heart sound can be heard appropriately. In order to illustrate capturing of the audio signal and amplifying the audio signal, FIG. 3 and FIG. 4 may be used as an example. Referring to FIG. 3, the heart sound captured without amplification, i.e., raw audio signal is shown.

Figure 4:
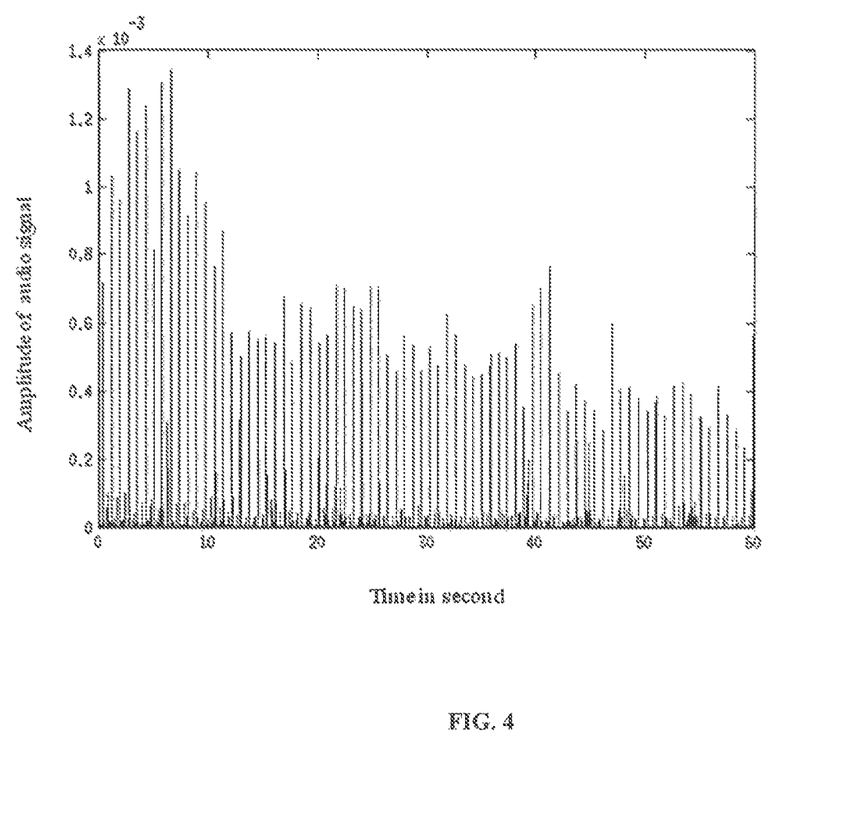
FIG. 4 shows the amplified audio signal after squaring, in accordance with an embodiment of the present disclosure.

After the audio signal is amplified, the audio signal may be further processed to detect an envelope of the amplified audio signal. In order to detect the envelope, the amplified audio signal may be squared. The audio signal may be squared in order to emphasize high amplitude components and diminish low amplitude components of the audio signal. For the amplified audio signal as shown in FIG. 3, upon squaring, the audio signal may be presented as shown in FIG. 4. After squaring the amplified audio signal, the audio signal may be filtered by applying a band pass filter.

Figure 5:
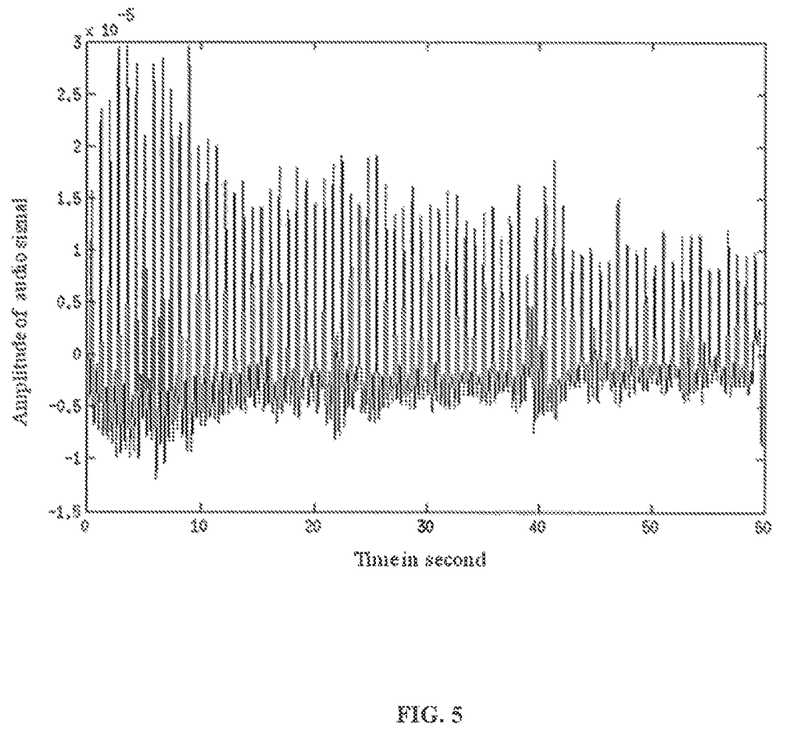
FIG. 5 shows the audio signal after applying band pass filter, in accordance with an embodiment of the present disclosure.

As the audio signal is captured externally, the audio signal comprises of all the frequencies in the human audible range (20 Hz to 20 kHz). Since, the frequency of the human heart beat sound is in a range of 0.7 Hz to 3.6 Hz in any circumstances, the signal is passed through a $2^{nd}$ order Butterworth band pass filter to capture the frequency present only in the range, i.e., 0.7 Hz to 3.66 Hz. For the audio signal squared, the audio signal after band pass filtering may be presented as shown in FIG. 5.

Subsequently, a Teager-Kaiser Energy Operator (TKEO) may be applied on the audio signal amplified upon squaring and applying the $2^{nd}$ order Butterworth band pass filter. The Teager-Kaiser energy operator is a nonlinear operator that calculates the energy of mono component audio signals as a product of the square of the amplitude and the frequency of the audio signal.

The energy of the audio signal, i.e., x(t) may be given by an equation $$E=\int_{-T}^{T}|x(t)|^2 dt$$

Figure 6:
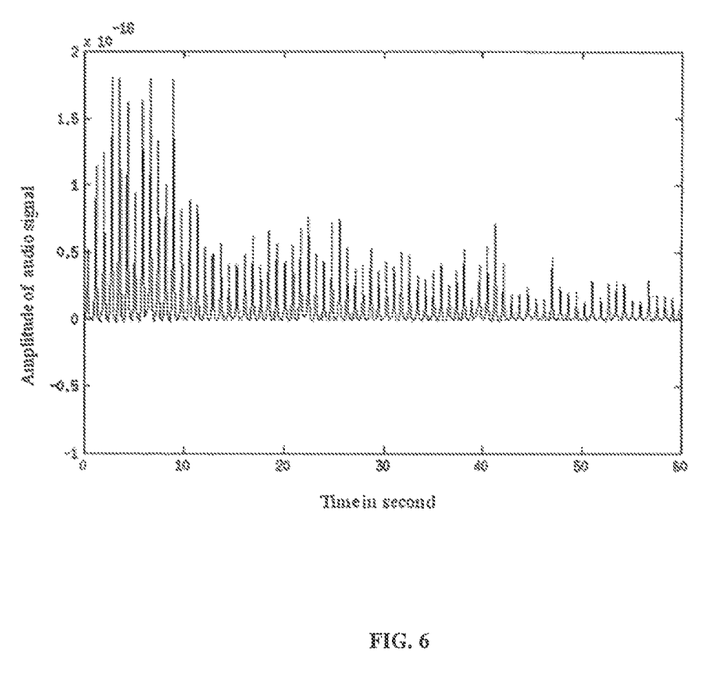
FIG. 6 shows the audio signal after applying the TKEO, in accordance with an embodiment of the present disclosure.

The energy of the audio signal may be obtained over a time 2T. Further, the energy of the audio signal may be estimated by using squared absolute value of the different frequency bands of Fourier transformed signal as a measure of the energy levels of respective bands. In order to estimate an instantaneous energy of the audio signal, an energy tracking operator, i.e., Teager-Kaiser Energy Operator (TKEO) may be used.

$$\psi c[x(t)] = [x'(t)]2 - x(t)''x(t)$$

where x(t) is the audio signal and x'(t) and x"(t) are its first and second derivatives respectively. The audio signal after applying the TKEO is shown in FIG. 6.

Figure 7:
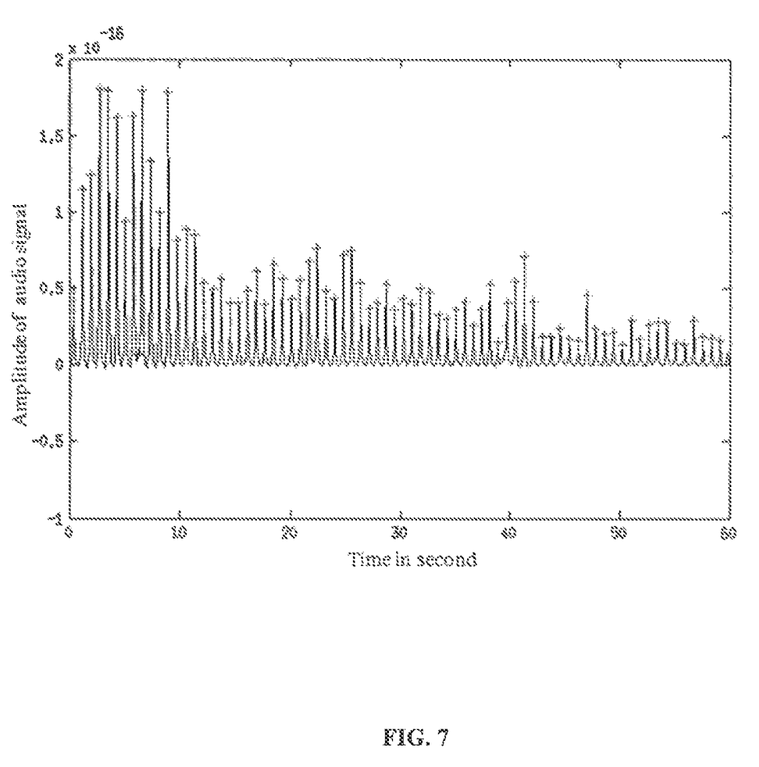
FIG. 7 shows peaks detected on the envelope of the time domain audio signal, in accordance with an embodiment of the present disclosure.

After applying the TKEO on the amplified audio signal and band passed, the envelope of the amplified audio signal may be detected. From the envelope, peaks of the audio signal, i.e., the energy spikes/magnitude may be detected. For calculating the peaks, an average of all earlier points from previously detected peak to current point is estimated. Subsequently, the magnitude of the current point is obtained. After obtaining the magnitude of the current point, the difference of the magnitude of the current point and the average of all earlier points from previous peak to the current point is calculated. In other words, the average of the all previous points is calculated from the previously detected peak. In another implementation, if the peak is not detected in the earlier points, an average of magnitude of points in the audio signal from initial value in processing window of the audio signal is considered. After calculating the difference, if the difference is greater than zero and the amplitude of the point subsequent to amplitude of the current point is equal or less, then the current point is considered to be a peak for the audio signal in time domain. Subsequently, the average is reset from the current point to detect new peak for subsequent magnitude of the points in the audio signal. Similarly, all the peaks are detected in the audio signal. The initial peaks detected on the envelope of the time domain audio signal are shown in FIG. 7.

After the peaks are detected, the peaks may have additional peaks. The peaks may be false positive peaks. In order to detect false positive peaks in the audio signal, a Fuzzy c Means (FCM) clustering algorithm may be used. The positive peaks may appear due to ambient noise identified as a peak that corresponds to the first heart sound, i.e., LUBB. The FCM clustering algorithm may be run to classify the peak to peak distances into two clusters. One cluster may comprise smaller peak to peak distance and second cluster may comprise higher peak to peak distance. The cluster comprising the higher peak to peak distance may correspond to correct peak to peak distances. The cluster comprising smaller peak to peak distance may correspond to the detection of false positives.

Figure 8:
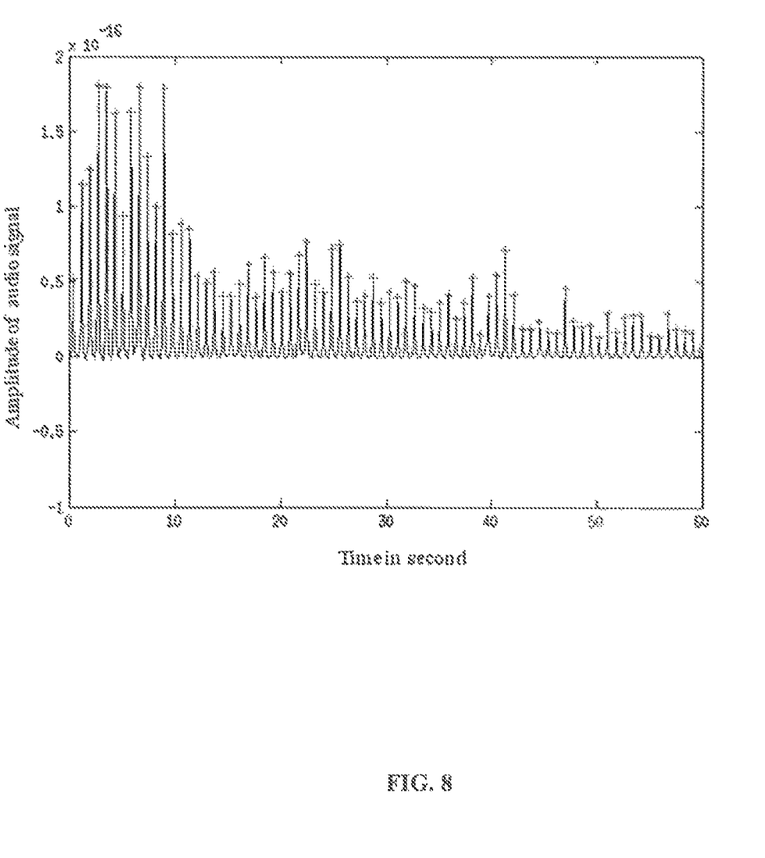
FIG. 8 shows peaks after peak correction on the time domain audio signal envelope, in accordance with an embodiment of the present disclosure.

The positive peaks may appear due to ambient noise identified as a peak that corresponds to the louder heart sound, i.e., LUBB or DUB depending upon the positioning of the electronic device. In order to correct the false positive peaks, a mean and a standard deviation of all the peak to peak distances that is present in the cluster having greatest compaction are calculated. Subsequently, every peak from a common peak that has an adjoining correct peak to peak distance may be inspected. After inspection, if the next detected peak value is less than the difference of the mean and the standard deviation, the next detected peak may be discarded as the false positive peak. Further, the mean and standard deviation of all peak to peak distances are calculated until a peak with the desired value greater than the (mean-standard deviation) is obtained. After identifying a true peak, the mean and standard deviation of all peak to peak distances are re-calculated and the process is again repeated from the next peak having an adjoining true peak and a false peak Further, from the cluster comprising the higher peak to peak distance, false negative peaks may be identified. The missed peaks may result in false negatives peaks. The missed peaks may occur when a louder heart sound or noise being followed by a less loud heart sound, due to difference in pressure applied on the chest while holding the electronic device by hand. In order to correct the false negative peaks, the region between the peaks, among which the distance has fallen in the cluster having highest centroid value, is identified. The peak detection is calculated between the two immediate local troughs following the points identified as peaks, between which the false peak is estimated to occur. FIG. 8 may be used to illustrate the peaks after peak correction on the time domain audio signal envelope.

Subsequently, a standard deviation $D_{std}$ of the entire dataset may be calculated. Based on the difference of the consecutive peaks detected, the heart rate of the individual may be determined. The consecutive difference of the detected peaks may correspond to an average time period of the heart beat. Subsequently, a reciprocal of the consecutive difference of the detected peaks may be calculated to determine the average heart rate of the individual.

Furthermore, based on the difference of the consecutive peaks detected, the heart rate variability of the individual may be determined. Specifically, the heart rate variability may be determined using time domain metrics of the audio signal. The heart rate variability may be determined by calculating a standard deviation of the consecutive peak to peak time differences. Further, a root mean square of the successive peak to peak time differences may be calculated. Further, a standard deviation between the successive differences of the consecutive peak to peak time differences may be calculated. Further, number of pairs of the successive peak to peak time difference that differ by more than 50 milliseconds may be calculated. Further, a proportion of the number of pairs of successive peak to peak time difference that differ by more than 50 milliseconds divided by the total number of peak to peak differences may be calculated. Further, the number of pairs of the successive peak to peak time difference that differ by more than 20 milliseconds may be calculated. Further, a proportion of the number of pairs of successive peak to peak time difference that differ by more than 20 milliseconds divided by the total number of peak to peak differences may be calculated. Based on the above conditions, the heart rate variability may be determined.

Figure 9:
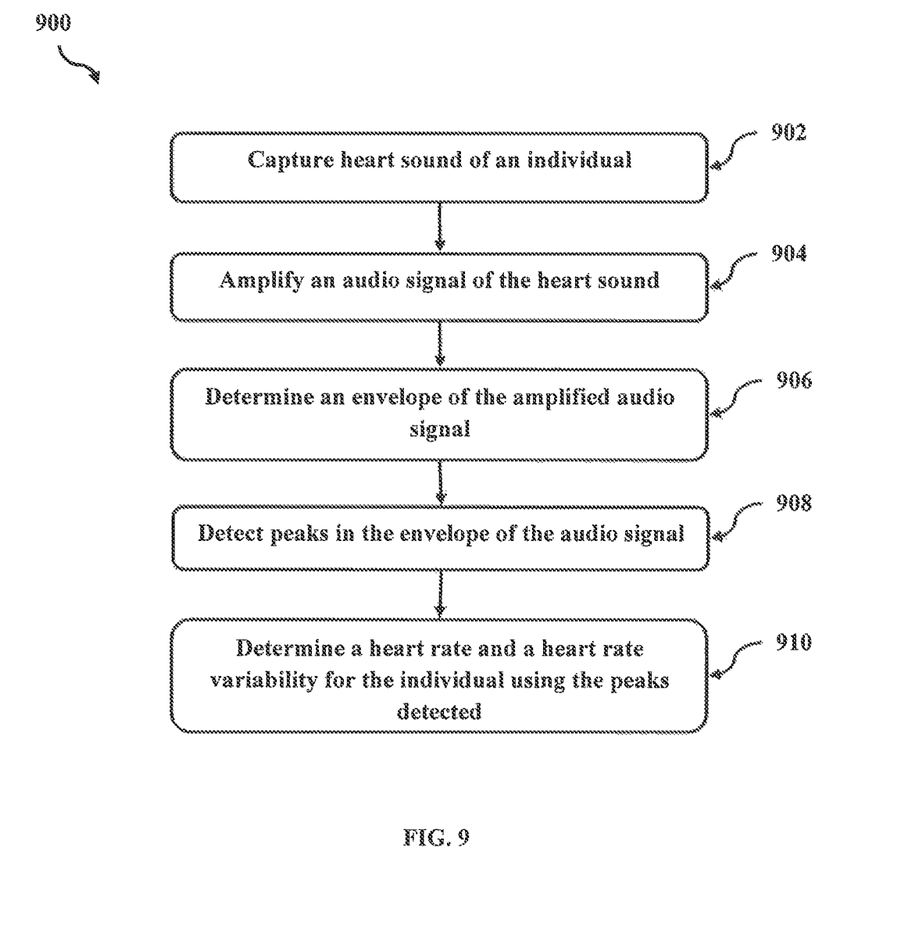
FIG. 9 shows a flowchart for determining a heart rate and a heart rate variability of an individual, in accordance with an embodiment of the present disclosure.

Referring now to FIG. 9, a method 900 for determining a heart rate and a heart rate variability of an individual is shown, in accordance with an embodiment of the present disclosure. The method 900 may be described in the general context of computer executable instructions. Generally, computer executable instructions can include routines, programs, objects, components, data structures, procedures, modules, functions, etc., that perform particular functions or implement particular abstract data types. The method 900 may also be practiced in a distributed computing environment where functions are performed by remote processing devices that are linked through a communications network. In a distributed computing environment, computer executable instructions may be located in both local and remote computer storage media, including memory storage devices.

The order in which the method 900 is described and is not intended to be construed as a limitation, and any number of the described method blocks can be combined in any order to implement the method 900 or alternate methods. Additionally, individual blocks may be deleted from the method 900 without departing from the spirit and scope of the disclosure described herein. Furthermore, the method may be implemented in any suitable hardware, software, firmware, or combination thereof. However, for ease of explanation, in the embodiments described below, the method 900 may be implemented in the above-described system 102.

At step/block 902, heart sound of an individual may be captured.

At step/block 904, an audio signal of the heart sound captured may be amplified.

At step/block 906, an envelope of the amplified audio signal may be detected. The envelope of the amplified audio signal may be detected by squaring of the audio signal amplified to obtain emphasized high amplitude components and diminished low amplitude components of the audio signal, applying a band pass filter on the audio signal (0.7-3.6 Hz) upon squaring, and applying a Teager-Kaiser Energy Operator (TKEO) on the audio signal filtered to obtain the envelope of the audio signal.

At step/block 908, peaks in the envelope of the audio signal may be detected. The peaks may be detected by calculating difference in magnitude of a point subsequent in the audio signal with an average of magnitude of earlier points in the audio signal from the last detected peak or the initial sample value in processing window of the audio signal when no peak is detected.

At step/block 910, a heart rate and a heart rate variability for the individual may be determined using the peaks detected.

Although implementations of system and method for determining a heart rate and a heart rate variability of an individual have been described in language specific to structural features and/or methods, it is to be understood that the appended claims are not necessarily limited to the specific features or methods described. Rather, the specific features and methods are disclosed as examples of implementations for determining a heart rate and a heart rate variability of an individual.

What is claimed is:

1. A method (1000) for determining a heart rate and a heart rate variability of an individual, the method (1000) comprising:
   capturing heart sound of an individual;
   amplifying, by a processor (202), an audio signal of the heart sound;
   detecting, by the processor (202), an envelope of the amplified audio signal, wherein the envelope of the amplified audio signal is detected by:
      squaring of the amplified audio signal to obtain emphasized high amplitude components and diminished low amplitude components of the audio signal;
      applying a filter on the audio signal upon squaring, wherein the filter is configured with a pass band of 0.7 to 3.6 Hz; and
      applying a Teager-Kaiser Energy Operator (TKEO) on the audio signal filtered to obtain the envelope of the audio signal;
   detecting, by the processor (202), peaks in the envelope of the audio signal, wherein the peaks are detected by:
      calculating difference in magnitude of a current point with an average of magnitude of earlier points in the audio signal from last detected peak or initial sample value in processing window of the audio signal when no peak is detected; and
      evaluating if (a) the difference is positive and (b) a next subsequent data point is equal to or lesser than the current point, in order to culminate in actually detecting that the current point is a peak;
   classifying, by the processor (202), peak to peak distance in the envelope into at least two clusters, to identify and correct false negative peaks and false positive peaks in the envelope of the audio signal; wherein the cluster comprising a higher peak to peak distance includes false negative peaks; and the cluster comprising a smaller peak to peak distance corresponds to detection of false positive peaks;
   correcting, by the processor (202), the false positive peaks by:
      calculating a mean and a standard deviation of all the peak to peak distances that are present in the cluster having smaller peak to peak distance;
      inspecting every peak from a common peak, that has an adjoining correct peak to peak distance;
      identifying if a next detected peak has a peak to peak distance less than the difference of the mean and the standard deviation; and
      discarding the next detected peak; and
   determining, by the processor (202), a heart rate and a heart rate variability for the individual using the peaks detected.

2. The method (1000) of claim 1, wherein classifying peak to peak distance in the envelope into at least two clusters comprises using a Fuzzy C Means (FCM) clustering.

3. The method (1000) of claim 1, wherein the heart rate of the individual is determined based on calculating an inverse of a difference of peak to peak time between two consecutive peaks within the envelope.

4. The method (1000) of claim 1, wherein the heart rate variability is determined by calculating one of a standard deviation of difference in peak to peak time between consecutive peaks within the envelope, a root mean square of difference in peak to peak time between successive peaks within the envelope, a standard deviation between successive differences of the consecutive peak to peak time differences, number of pairs of successive peak to peak time difference differing by more than 50 milliseconds, a proportion of the number of pairs of successive peak to peak time difference differing by more than 50 milliseconds over a total number of peak to peak differences, a number of pairs of successive peak to peak time difference that differ by more than 20 milliseconds, and a proportion of the number of pairs of successive peak to peak time difference that differ by more than 20 milliseconds divided by the total number of peak to peak differences.

5. A system (102) for determining a heart rate and a heart rate variability of an individual, the system (102) comprising:
a memory (206); and
a processor (202) coupled to the memory (206), wherein the processor (202) executes program instructions stored in the memory (206), to:
capture heart sound of an individual;
amplify an audio signal of the heart sound;
detect an envelope of the amplified audio signal, wherein the envelope of the amplified audio signal is detected by:
squaring of the amplified audio signal to obtain emphasized high amplitude components and diminished low amplitude components of the audio signal;
applying a filter on the audio signal upon squaring, wherein the filter is configured with a pass band of 0.7 to 3.6 Hz; and
applying a Teager-Kaiser Energy Operator (TKEO) on the audio signal filtered to obtain the envelope of the audio signal;
detect peaks in the envelope of the audio signal, wherein the peaks are detected by;
calculating difference in magnitude of a current point in the audio signal with an average of magnitude of earlier points in the audio signal from last detected peak or initial sample value in the processing window of the audio signal when no peak is detected; and
evaluating if (a) the difference is positive and (b) a next subsequent data point is equal to or lesser than the current point, in order to culminate in actually detecting that the current point is a peak;
classify peak to peak distance in the envelope into at least two clusters, to identify and correct false negative peaks and false positive peaks in the envelope of the audio signal; wherein the cluster comprising a higher peak to peak distance includes false negative peaks; and the cluster comprising a smaller peak to peak distance corresponds to detection of false positive peaks;
correct the false positive peaks by:
calculating a mean and a standard deviation of all the peak to peak distances that are present in the cluster having smaller peak to peak distance;
inspecting every peak from a common peak, that has an adjoining correct peak to peak distance;
identifying if a next detected peak has a peak to peak distance less than the difference of the mean and the standard deviation; and
discarding the next detected peak; and
determine a heart rate and a heart rate variability for the individual using the peaks detected.

6. The system (102) of claim 5, wherein the processor classifies peak to peak distance in the envelope into at least two clusters using a Fuzzy C Means (FCM) clustering.

7. The system (102) of claim 5, wherein the heart rate of the individual is determined based on calculating an inverse of a difference of peak to peak time between two consecutive peaks within the envelope.

8. The system (102) of claim 5, wherein the heart rate variability is determined by calculating one of a standard deviation of difference in peak to peak time between consecutive peaks within the envelope, a root mean square of difference in peak to peak time between successive peaks within the envelope, a standard deviation between successive differences of the consecutive peak to peak time differences, number of pairs of successive peak to peak time difference differing by more than 50 milliseconds, a proportion of the number of pairs of successive peak to peak time difference differing by more than 50 milliseconds over a total number of peak to peak differences, a number of pairs of successive peak to peak time difference that differ by more than 20 milliseconds, and a proportion of the number of pairs of successive peak to peak time difference that differ by more than 20 milliseconds divided by the total number of peak to peak differences.

9. The system (102) of claim 5, wherein the heart sound is captured using a microphone.

10. A computer program product comprising a non-transitory computer readable medium having a computer readable program embodied therein, wherein the computer readable program, when executed on a computing device, causes the computing device to:
capture heart sound of an individual;
amplify an audio signal of the heart sound;
detect an envelope of the amplified audio signal, wherein the envelope of the amplified audio signal is detected by:
squaring of the amplified audio signal to obtain emphasized high amplitude components and diminished low amplitude components of the audio signal;
applying a filter on the audio signal upon squaring, wherein the filter is configured with a pass band of 0.7 to 3.6 Hz; and
applying a Teager-Kaiser Energy Operator (TKEO) on the audio signal filtered to obtain the envelope of the audio signal;
detect peaks in the envelope of the audio signal, wherein the peaks are detected by;
calculating difference in magnitude of a current point in the audio signal with an average of magnitude of earlier points in the audio signal from last detected peak or initial sample value in the processing window of the audio signal when no peak is detected; and
evaluating if (a) the difference is positive and (b) a next subsequent data point is equal to or lesser than the current point, in order to culminate in actually detecting that the current point is a peak;
classify peak to peak distance in the envelope into at least two clusters, to identify and correct false negative peaks and false positive peaks in the envelope of the audio signal; wherein the cluster comprising a higher peak to peak distance includes false negative peaks; and the cluster comprising a smaller peak to peak distance corresponds to detection of false positive peaks;
correct the false positive peaks by:
calculating a mean and a standard deviation of all the peak to peak distances that are present in the cluster having smaller peak to peak distance;
inspecting every peak from a common peak, that has an adjoining correct peak to peak distance;
identifying if a next detected peak has a peak to peak distance less than the difference of the mean and the standard deviation; and
discarding the next detected peak; and
determine a heart rate and a heart rate variability for the individual using the peaks detected.

* * * * *